(12) United States Patent
Krumme et al.

(10) Patent No.: US 7,899,149 B2
(45) Date of Patent: Mar. 1, 2011

(54) NON-CONTACTING ROTARY JOINT WITH CLOCK MODULATION

(75) Inventors: Nils Krumme, Feldafing (DE); Georg Lohr, Eichenau (DE); Stephan Lindorfer, Müchen (DE)

(73) Assignee: Schleifring und Apparatebau GmbH, Fürstenfeldbruck (DE)

( * ) Notice: Subject to any disclaimer, the term of this patent is extended or adjusted under 35 U.S.C. 154(b) by 0 days.

(21) Appl. No.: 12/565,440

(22) Filed: Sep. 23, 2009

(65) Prior Publication Data

US 2010/0091935 A1    Apr. 15, 2010

(30) Foreign Application Priority Data

Oct. 9, 2008    (DE) .................. 10 2008 042 697

(51) Int. Cl.
*H05G 1/60* (2006.01)
(52) U.S. Cl. .............................. 378/4; 378/15
(58) Field of Classification Search ................ 378/4, 15, 378/19
See application file for complete search history.

(56) References Cited

U.S. PATENT DOCUMENTS

| | | | |
|---|---|---|---|
| 6,396,613 B1 * | 5/2002 | Harrison et al. ............. 398/141 |
| 6,862,299 B2 | 3/2005 | Popescu | |
| 6,975,148 B2 | 12/2005 | Miyata et al. | |
| 7,295,594 B1 | 11/2007 | Lohr | |
| 7,717,619 B2 * | 5/2010 | Katcha et al. ................. 378/197 |
| 2001/0055362 A1 * | 12/2001 | Takanashi et al. ............. 378/15 |

FOREIGN PATENT DOCUMENTS

EP    1094381 A2 *    4/2001

* cited by examiner

*Primary Examiner* — Irakli Kiknadze
(74) *Attorney, Agent, or Firm* — Meyertons, Hood, Kivlin, Kowert & Goetzel, P.C.; Eric B. Meyertons

(57) ABSTRACT

A non-contacting data path for rotating data transmission of digital data from a data source to a data sink includes at least one clock modulator. A data clock frequency is specifically modulated with the clock modulator to widen a spectrum of data signals and achieve improved EMC properties in measurements according to valid EMC Standards. Owing to use of a plurality of clock modulators along a course of a non-contacting rotary transmission path, signal jitter caused by individual components of the data transmission path is in each case replaced by artificially caused jitter of clock modulation. Thus, data transmission with defined jitter and defined signal quality can be achieved.

15 Claims, 4 Drawing Sheets

NON-CONTACTING ROTARY JOINT WITH CLOCK MODULATION

PRIORITY CLAIM

This application claims priority to pending German Patent Application 10 2008 042 697.0 filed on Oct. 9, 2008.

BACKGROUND OF THE INVENTION

1. Field of the Invention

The invention relates to a data transmission system for transmitting data between a rotating part and a stationary part, in particular between the rotating part and the stationary part of a computer tomograph, and also to a computer tomograph having a corresponding transmission system.

2. Description of the Relevant Art

With rotatable units such as radar installations or also computer tomographs, and also with linearly movable units such as crane and conveyor systems, it is necessary to transmit electrical signals or energy between units that are moveable relative to each other. For this, usually a conductor structure is provided in a first unit, and a suitable tap in a second unit. In the following explanations the term conductor structures relates to all conceivable forms of conductor structures which are suitable for conducting electrical signals. This also relates to known contacting slide paths or slip rings. Essential for transmission by means of rotary joints or linear "slide tracks" which also may be designed to be non-contacting is a small distance of transmission between the units that are rotatable relative to each other. Thus, a signal can be coupled-out optionally by means of a contacting connection, or without contact in the near field of a conductor structure.

From U.S. Pat. No. 6,433,631 B2 a device is known for data transmission in computer tomographs. A transmitted signal is applied to a strip line in a rotating part. On the stationary part a tap is provided which is guided along at a small distance of about 1 mm from the strip line. With computer tomographs the length of the strip lines is of an order of magnitude of about 5 meters. Thus, for data transmission rates of a few tens of gigabytes per second, signals must be conducted with a bandwidth of several gigahertz via a conductor system of about 5 meters length. This conductor system cannot be screened because it extends along a rotation gap. With increasing frequencies it becomes increasingly difficult to keep the radiation of high-frequency interference into free space below admissible limiting values.

In US 2004/0165652 it is suggested that the spectrum of the transmitted signals be modified. For this, special signals which are encoded with pseudo-random numbers are transmitted. Thereby the spectral power density of the signals is reduced.

In U.S. Pat. No. 6,862,299 B2 the use of clock regeneration circuits is suggested for improving signal quality from the optical data path.

SUMMARY OF THE INVENTION

In an embodiment a rotary data transmission system particularly for computer tomographs is provided, in which more favorable measured EMC values are achieved, or interference emissions are reduced in conformity with applicable EMC Standards.

Another embodiment provides a computer tomograph including a rotary data transmission system of this kind.

In an embodiment, a clock modulator for broadening a frequency spectrum of a data clock so that further spectral spikes occur in close proximity of individual spectral spikes of an unmodulated data clock is provided, whereby signal amplitudes of individual spectral spikes are reduced.

Another embodiment provides a method for transmitting data via a rotary joint, in which signal quality is improved.

In an embodiment a rotating data transmission path includes:
a rotating part;
a stationary part; and
a rotary joint with a transmission line arrangement and a receiving coupler arrangement for transmission of signals between the rotating part and the stationary part;
with the rotating part including;
at least one data source with a first transmitter, for generating a digital data stream;
at least one first line for relaying the digital data stream from the first transmitter; and
at least one driver with a first receiver for receiving the digital data stream along the first line, and for controlling the transmission line arrangement;
and with the stationary part including:
at least one receiving unit for receiving and conditioning signals of a data stream received via the receiving coupler arrangement, having a second transmitter for retransmitting the data stream;
at least one second line for relaying the data stream retransmitted from the second transmitter; and
at least one data sink with at least one second receiver for receiving the retransmitted data stream along the second line;
wherein at least one of the data source, driver, receiving unit, and data sink include a clock modulator for broadening a frequency spectrum of a data clock, so that further spectral spikes occur in close proximity of individual spectral spikes of an unmodulated data clock, whereby a signal amplitude of the individual spectral spikes is reduced.

In an embodiment, the above embodiments are also achieved with a computer tomograph including a rotating data transmission path of the above kind.

In an embodiment, the above embodiments are also achieved with a clock modulator for broadening a frequency spectrum of a data clock so that further spectral spikes occur in close proximity of individual spectral spikes of an unmodulated clock, whereby a signal amplitude of the individual spectral spikes is reduced. The clock modulator includes an integrated PLL (Phase Locked Loop) component in which a modulation voltage from a modulation generator is fed into an output terminal of a filter capacitor in a loop filter.

Alternatively, the clock modulator includes an integrated PLL component in which optionally a supply voltage of a VCO (Voltage Controlled Oscillator), or a supply voltage of an entire PLL component, is changed by a modulation voltage from a modulation generator.

In an embodiment a method for transmitting data via a rotary joint, includes:
converting data from a data source to signals by means of a first transmitter with optional clock modulation;
transmitting the signals by means of a first line to a driver;
receiving the signals with a first receiver in the driver;
feeding signals from the driver with optional clock modulation into a transmission line arrangement of the rotary joint;
receiving signals from the transmission line arrangement by means of a receiving coupler arrangement;
evaluating signals received by the receiving coupler arrangement in a receiving unit and converting these signals, with optional clock modulation, to signals by means of a second transmitter;

transmitting the signals by means of a second line to a data sink; and receiving the signals with optional clock modulation with a second receiver in the data sink.

BRIEF DESCRIPTION OF THE DRAWINGS

In the following the invention will be described by way of example, without limitation of the general inventive concept, on examples of embodiment and with reference to the drawings.

Figure 1:
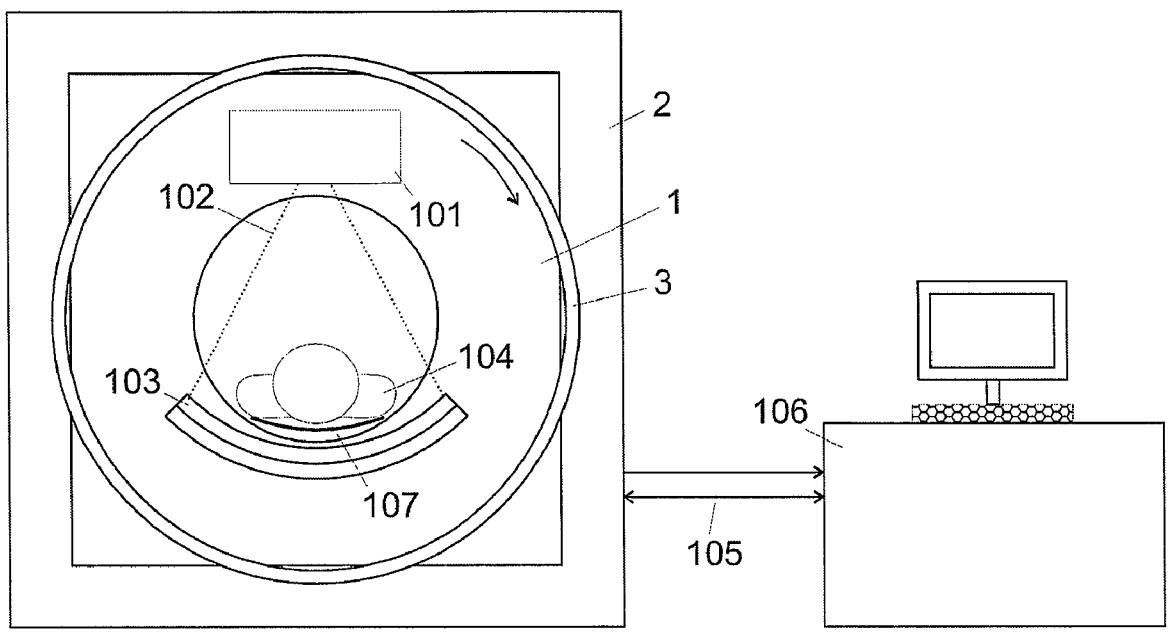
FIG. 1 schematically shows in a general form a computer tomograph.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

FIG. 1 shows a device according to the invention on an example of a computer tomograph. The computer tomograph (CT scanner) includes two main mechanical parts. A stationary part 2 serves as a base and support of the entire instrument, in which the rotating part 1 rotates. A patient 104 is positioned on a berth 107 in the opening of the rotating part. An X-ray tube 101 and also a detector 103 disposed opposite thereto are provided for scanning the patient by means of X-rays 102. The X-ray tube 101 and the detector 103 are disposed to be rotatable on the rotating part 1. A rotary joint 3 serves for electrical connection between the rotating part 1 and the stationary part 2. With this, on the one hand the high electrical power for feeding the X-ray tube 101 is transmitted in the direction of the rotating part 1, and simultaneously the raw data of the image are transmitted in the opposite direction. Parallel to this, communication of control information in both directions is provided. An evaluation and control unit 105 serves for operating the computer tomograph and also for displaying generated images. Communication with the computer tomograph is effected via a bidirectional link 105.

Figure 2:
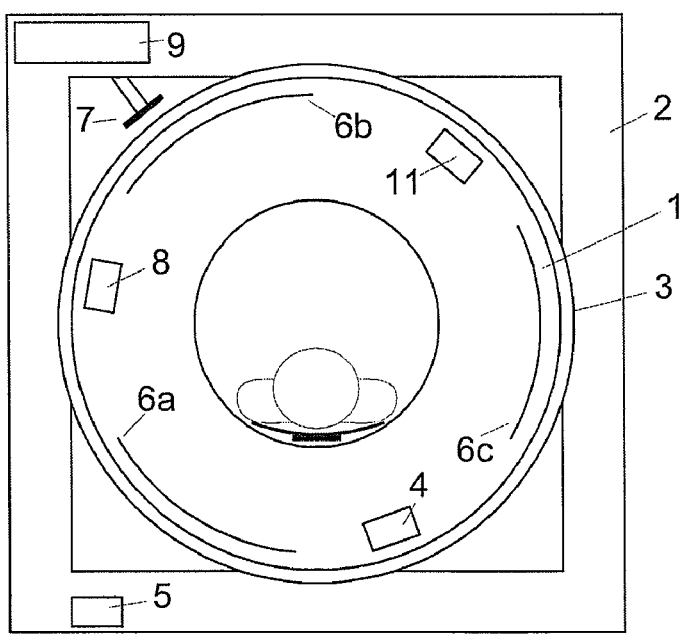
FIG. 2 schematically shows a data transmission system.

FIG. 2 shows in simplified form an example of an arrangement of a data transmission system. The data from a data source 4 (detector 103 with subsequent signal processing or DAS) on the rotating part 1 are conditioned with a first transmission means 8 and relayed to the transmission line arrangement which here is illustrated by way of example as comprising three parts 6a, 6b, 6c. This transmission line arrangement now conducts the high-frequency signals. These are tapped-off by the receiving coupler arrangement 7. A receiving coupler arrangement which is fixedly connected with the stationary frame is illustrated by way of example. The signals intercepted by this receiving coupler arrangement 7 are relayed to a first receiving means 9 for conditioning. Output signals from the latter are then conducted to a data sink 5.

Figure 3:
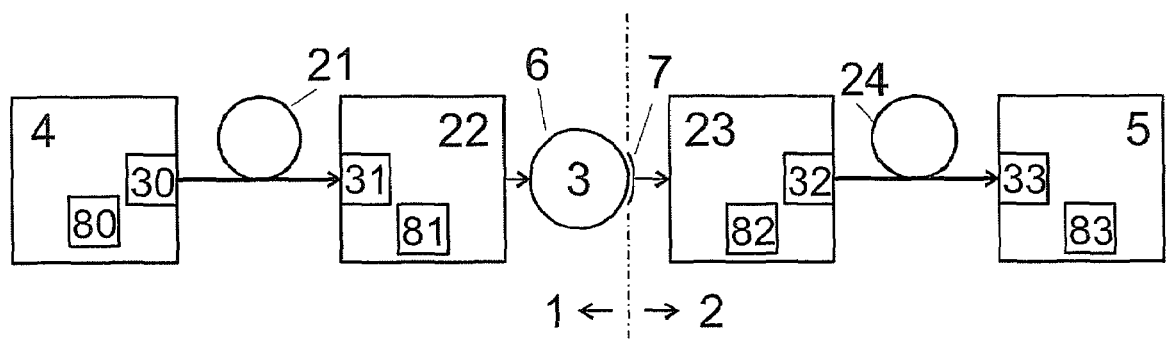
FIG. 3 shows a block circuit diagram of a computer tomograph.

FIG. 3 shows a block circuit diagram of a computer tomograph. On the rotating side 1 of the computer tomograph, signals from the data source 4 are relayed to the driver 22 by means of a first line 21. For this, a first transmitter 30 is provided in the data source 4, and a first receiver 31 in the driver 22. The driver 22 feeds the transmission line arrangement 6 of the rotary joint 3. The transmission line arrangement 6 can be an electrical transmission line arrangement such as, for example, a strip line. As an alternative to this, the transmission line arrangement can be also a light-waveguide, for example a mirror coated trench, or a glass fiber, or a synthetic material fiber. The driver 22 is also designed according to the transmission line arrangement. Thus, in the case of an optical transmission line arrangement it includes an optical transmitter, and in the case of an electrical transmission line arrangement an electrical transmitter. On the stationary side 2 of the computer tomograph the signals from the transmission line arrangement are tapped-off by means of a receiving coupler arrangement. The receiving coupler arrangement 7 is matched to the transmission line arrangement and is optionally an electrical or optical coupler. The receiving unit 23 picks up the signals from the receiving coupler arrangement and, in the case of optical signals, converts these to electrical signals. The electrical signals are then further conditioned within the receiving unit 23, for example amplified, and/or filtered, and/or digitized. Finally these signals are transmitted via a second transmitter 32 by means of a second line 24 to a second receiver 33 in the data sink. A clock modulator 80, 81, 82, 83 is provided in at least one of the data source 4, the driver 22, the receiving unit 23, and the data sink 5.

Figure 4:
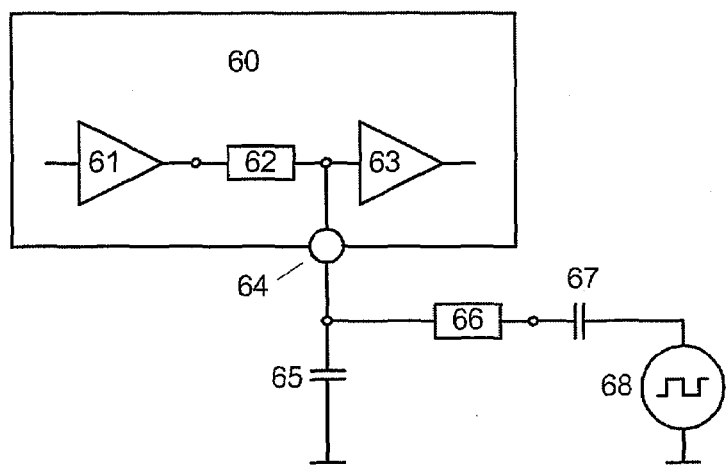
FIG. 4 shows a coupling-on of the filter of a PLL.

FIG. 4 shows a coupling-on to the filter of a PLL. An integrated PLL component 60 has a filter between the phase comparator and the VCO. This filter includes a first amplifier 61 or driver with a series resistor 62 connected to follow in series. A second amplifier 63 for high-ohm tapping-off the signal to the subsequent steps of the circuit is provided at the series resistor. The point between the resistor and the second amplifier is led out of the chip or housing via an external terminal pin 64. An external filter capacitor 65 is coupled to this terminal pin 64. According to an embodiment, a modulation signal from a modulation signal generator 68 is here fed-in via a coupling capacitor 67 and a series resistor 66. The fed-in signal is superposed on the internal phase regulating signal and thus serves for modulation of the VCO frequency.

Figure 5:
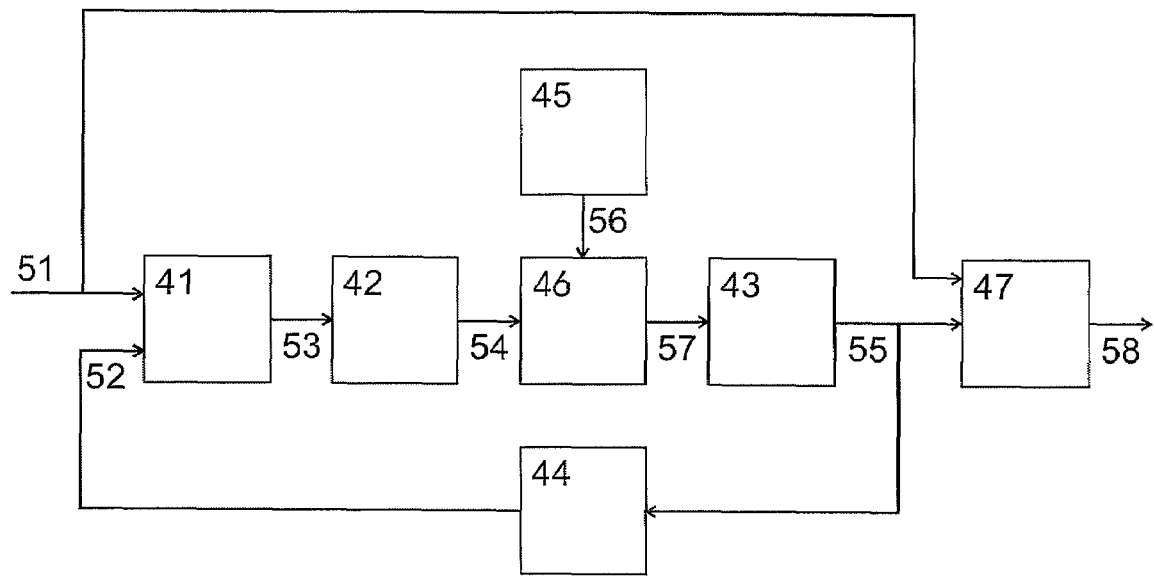
FIG. 5 shows a special embodiment of a clock modulator.

FIG. 5 shows a special embodiment of a clock modulator. An input signal from a data clock 51 is compared with a frequency-divider output signal 52 in the phase comparator 41. The phase comparator can be also a frequency comparator or a combined frequency/phase comparator. The output signal 53 of the phase comparator is passed to a filter 42 (loop filter) and there typically subjected to a low-pass filtering. The output signal 56 of the modulation generator 45 is added to the output signal 54 of the filter 42 in the adder 46, and the sum signal 57 is passed to the VCO 43. The output signal 55 of the VCO corresponds to a modulated data clock. The transmitted data can now be synchronized with the modulated data clock, for example by means of a flip-flop 47. Thus, the signal is given a new modulated clock. Instead of the flip-flop 47, any other known synchronization element can be used. The clock-modulated data signal 58 at the output of the flip-flop can then be passed on.

Figure 6:
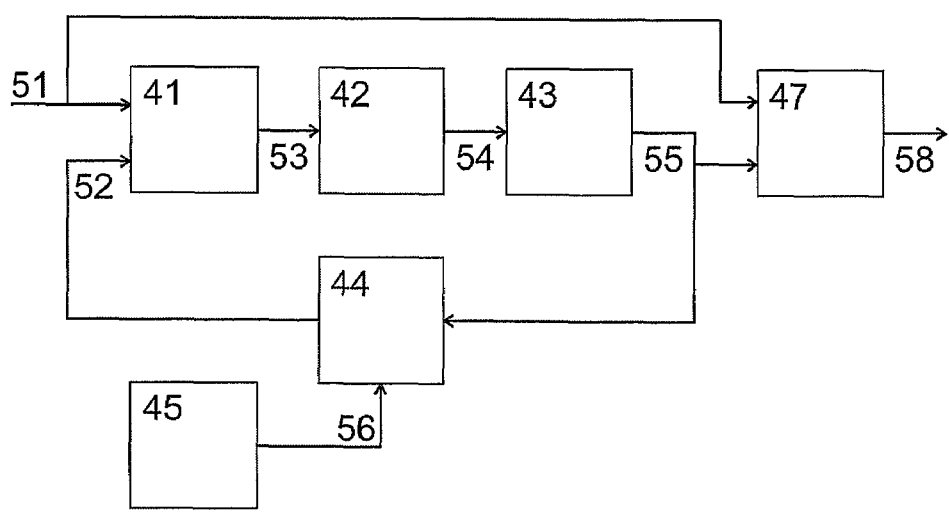
FIG. 6 shows another embodiment of a clock modulator.

FIG. 6 shows a similarly built-up circuit. However, contrary to FIG. 5 here the division ratio of the frequency divider 44 is controlled by the output signal 56 of the modulation generator 45. In this case the output signal of the modulation generator can be also a digital signal which switches-over between various dividing factors.

Figure 7:
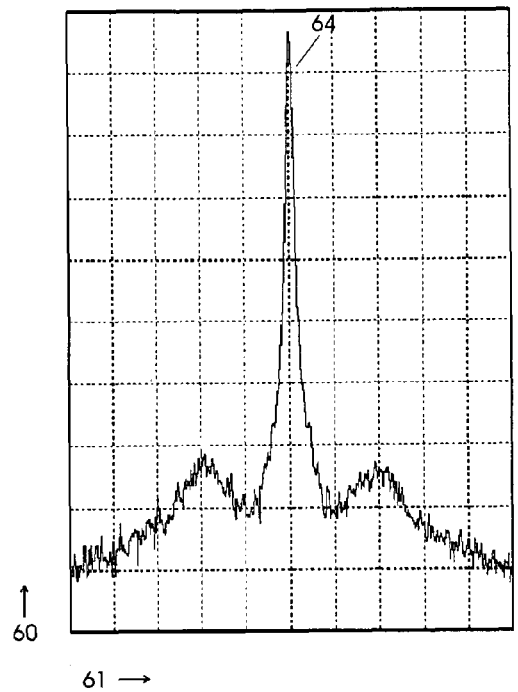
FIG. 7 shows a cut-out portion of the spectrum of a signal without clock modulation.

FIG. 7 shows a cut-out portion of a spectrum of a typical conventional signal without clock modulation. The axis 61 represents the frequency, and the axis 60 represents the amplitude on a logarithmic scale. The center of the illustration along the linear frequency axis is located at a frequency of 5 GHz. The frequency axis is divided into 10 steps, each of 500 kHz. The logarithmic scale of the amplitude axis 60 is 5 dB for each of the 10 parts, with the signal amplitude at the upper end of the Figure being −25 dBm, and at the lower end of the Figure being −75 dBm. The spectrum is derived from a typical signal of a modern data transmission path with low jitter. The amplitude of the single peak at the intermediate frequency of 5 GHz is at about −26 dBm.

Figure 8:
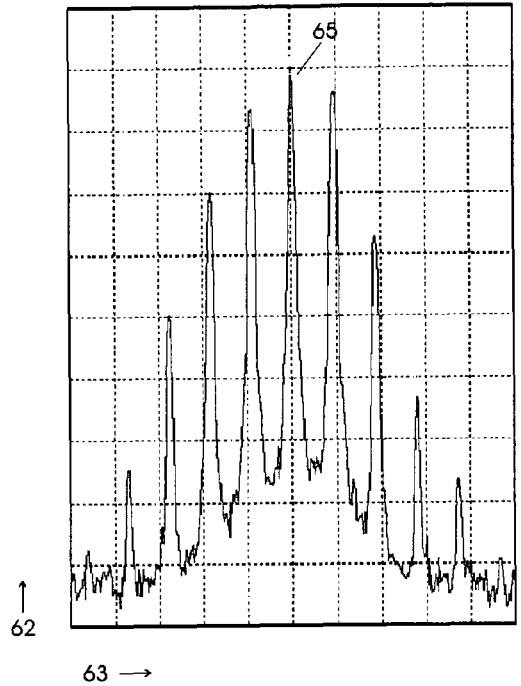
FIG. 8 shows a cut-out portion of the spectrum of a signal with clock modulation.

FIG. 8 shows a diagram of a signal of a clock modulator on the same scale as in FIG. 7. For this, the amplitude is represented on the axis 62 on the same scale as in FIG. 7, and the frequency is represented on the axis 63 also on the same scale as in FIG. 7. Owing to the frequency modulation, a spectrum now results with a multitude of spikes around the central spike 65. As the total power of the signal remains constant but is now distributed amongst a plurality of spikes, the total amplitude becomes less. Here the amplitude of the largest spike 65 is at −30 dBm, i.e. 4 dB lower than in FIG. 7. Thus, with a signal of this kind the measured EMC values can be reduced by 4 dB. Of course, with stronger modulation the individual spikes can be reduced further, and the measured EMC values further improved.

A rotary joint 3 in accordance with the invention comprises a transmission line arrangement 6 which is disposed on a rotating part 1 preferably along the circumference. The transmission line arrangement 6 is fed by a driver 22. The transmission line arrangement includes at least one line for conducting electro-magnetic waves, which is mounted preferably along at least one circular segment or a circular track on the rotating part. The transmission line arrangement may include, for example, mechanical slip-rings, non-contacting electrical coupling elements such as inductive or capacitive coupling elements, or also light-waveguides. Similarly, the transmission line arrangement can include a combination of a plurality of different coupling elements. If the transmission line arrangement is an electrical line such as a strip line, then the driver 22 includes an electrical driver. A driver is here understood to be a circuit for adapting the signals at their input so that they can be fed into the transmission line arrangement. Thus it must be possible to feed electrical energy at a given signal amplitude into the given impedance of the transmission line arrangement. As an alternative to this, the transmission line arrangement may be also a light-waveguide, for example a glass fiber or also a synthetic material fiber. Similarly, the transmission line arrangement may be also designed as a mirror trench. In the case of an optical transmission line arrangement, the driver 22 includes a light source which converts electrical input signals to optical output signals.

A receiving coupler arrangement 7 is disposed to be opposite to the rotating part, e.g., on the stationary part 2. It is designed to tap signals from the transmission line arrangement 6. Accordingly it is configured to be an electrical or optical coupler. The signals from the receiving coupler arrangement 7 are conducted to a receiving unit 23. This receiving unit converts optical to electrical signals, if necessary, amplifies the signals from the receiving coupler arrangement, and conditions the signals, if necessary.

Typically at least one line 21, 24 is provided for connection between a data source 4 and the driver 22, and/or between the receiving unit 23 and the data sink 5. This line can be an electrical line, but preferably a light-waveguide. Thus, for example, the connection between the data source 4 and the driver 22 can be effected by means of light-waveguides, while in the same arrangement the connection between the receiving unit 23 and the data sink 5 is designed as an electrical connecting line. Similarly, also the electrical and the optical connection can be interchanged. Alternatively, also two optical connections can be employed. Transmitters 30, 32 and also receivers 31, 33 are provided to adapt the signals to the line 21, 24. In the case of an optical line, an optical transmitter and receiver are used, while in the case of an electrical line, an electrical transmitter and receiver are to be used.

All electrical components used in the arrangement, in particular the transmission line arrangement, but also the electrical lines 21, 24, and even the transmitters 30, 32 and receivers 31, 33, emit high-frequency energy.

For an assessment of the EMC properties of a rotary joint, typically a measurement of radiated high-frequency energy is performed in conformity with a standard, such as for example CISPR 11. For this, the entire radiated high-frequency energy of the device is taken into account.

In an assessment in conformity with CISPR 11, the frequency spectrum to be analyzed is divided into individual spectral regions having a bandwidth of 100 kHz, and the spectral power in a region of this kind is determined. During a given period of measurement, for example 100 ms, the peak signal value in each of these frequency regions is measured. With digital signals as typically transmitted along digital data paths, the frequency spectrum is spike-shaped (peaked). According to the coding used or the data transmitted, individual discrete spikes or a broad band of adjacent spikes will appear. The driver 22 for controlling the transmission line arrangement 3, and also the transmitters (30, 32), emit a given output signal amplitude of the square-wave signal independently from the data content. If now owing to the signal a multitude of spikes appear at different frequencies, then their total power is just as high as the power of a single spike in the case of a corresponding signal emitted only in a narrow band. Thus, the amplitude of this single spike is distinctly higher. Relevant for compliance with an EMC Standard is whether the emitted signals fall below a given limiting value. If now the entire high-frequency energy is distributed not in a narrow band, e.g., in the shape of a spike, but instead in a broader frequency band, e.g., among many spikes, then these many spikes have lower amplitudes, and the limiting value can be maintained more easily. A prerequisite for this is that the individual spikes are spread apart sufficiently and are not all located in the same spectral region of the measurement.

Modern high-speed transmission systems attempt to maintain signal quality as high as possible, and therewith to maintain jitter of the signal to be transmitted as low as possible in order to achieve as low as possible a bit error rate. For this, in accordance with prior art, PLLs are made use of for frequency synchronization. Now a data signal having a frequency which has been synchronized or stabilized by a PLL of this kind has a marked discrete spectrum with a few individual discrete spikes. The better the PLL operates, the more narrow are the spikes. Thus, U.S. Pat. No. 6,862,299 also describes an arrangement which uses a plurality of PLLs along the course of a data path. This makes possible an excellent signal quality, but is counter-productive as far as EMC properties are concerned.

Now according to the embodiments disclosed herein, a signal to be transmitted is modulated in at least one place in the signal path, so that the frequency spectrum is broadened. Instead of one single spike a plurality of spikes now arise, all of which have a lower amplitude than the previous single spike. Laboratory measurements have shown that a reduction of the amplitude of all spikes by 6 dB is made possible by a modulation of this kind. If a modulated signal of this kind is represented in a temporal region, then of course it will have a distinctly higher jitter than an optimal signal. However, modern receivers having modern PLLs are also able to evaluate strongly jittered signals. The clock modulation is effected preferably by means of one clock modulator (80, 81, 82, 83). The term spike (peak) is here used for a narrow band signal portion which in a spectral representation, for example on a spectrum analyzer, is shown to be spike-shaped.

In an embodiment, clock modulators (80, 81, 82, 83) are located at various positions along the signal path. Thereby an even higher transmission quality can be achieved. Owing to each of the various components in the signal path, such as supply leads or light-waveguides 21, 24, and also the corresponding drivers or electro-optical or opto-electronic converters, additional jitter is caused in the transmission path. If now for example a clock modulator is used in the first transmitter 30, then a signal that is of widened spectrum and therefore more favorable for EMC measurements can be transmitted through the first line 21. In addition, further jitter of the first receiver 31 and the first line 21 is added to the jitter generated by the clock modulator. If the signal is now transmitted further as far as the data sink 5, then jitter of all further components, and in particular jitter of the rotary joint 3, is added to this jitter. In order to improve transmission quality substantially and to reduce jitter, a further clock modulator 81 can be incorporated in the driver 22, for example. This ensures that the jitter of the output signal now corresponds only to the jitter given by the clock modulator, and is reduced by the amount of jitter generated additionally by the components 30, 31 and 32. Finally, once more another clock modulator 82 can be used in the receiving unit 23, or also in the second transmitter 32. This again reduces the jitter of the signal by the amount of jitter introduced by the components located in circuit to follow the last clock modulator.

It is of special advantage for a clock modulator 80, 81, 82, 83 to comprise a PLL, with an additional modulation signal 56 being applied to the analog input of the VCO 43. It is preferred to add this additional modulation signal to the output signal 42 of the filter connected to follow the phase detector 41. However, basically any other combinatorial or transmission function is possible.

Furthermore, it is of advantage for the clock modulator to have a PLL, with the division ratio of the frequency divider 44 located between the VCO 43 and the phase comparator 41 being adjustable by a modulation generator 45. In this, the division ratio can be changed in a few fixed steps, or also quasi-linearly.

The clock modulators in accordance with the invention can be also incorporated with further components of the arrangement. Thus, for example, a clock modulator 80 can be incorporated with the first transmitter 30 or the data source 4. Similarly, a second clock modulator can be incorporated with the first receiver 31 and/or the driver 22. Furthermore, a third clock modulator 83 can be incorporated with the receiving unit 23 and/or the second transmitter 32. Finally, also a fourth clock modulator 84 can be incorporated with the second receiver 33 or the data sink 5. Basically, further clock modulators also can be provided.

It is an advantage for the clock modulator to be of adjustable modulation frequency, and/or modulation voltage, or modulation amplitude. It is especially favorable for a modulation generator to be a delta signal generator. The delta signal then can be fed advantageously into the control input of the VCO. The frequency variation of the VCO can then be preset by the signal amplitude of the delta voltage.

Highly-integrated components already containing a PLL are frequently on the market, such as for example optical transmitters, receivers, transceivers, or clock recovery circuits. Often the control voltage input terminal of the VCO is not directly accessible. However, frequently a terminal for a smoothing capacitor or filter capacitor serving to define the frequency response is provided. A modulator voltage from the modulation generator 45 can be applied also externally to this input terminal in order to achieve a modulation of the output signal. A capacitive coupling-on is here of special advantage. Even if an input terminal of this kind is not present, then in many cases a modulation of the output signal can be still achieved by varying the supply voltage of the complete PLL according to the modulation signal. Owing to fluctuations of the supply voltage, the output frequency of the VCO also changes. With a digitally controllable PLL the division ratio of the frequency divider 44 also can be varied, or at least switched-over between two values.

The modulation frequency can be in a range which can be still controlled by the circuit of the VCO. Especially preferred is a range from 100 Hz to 10 MHz. During use of a data clock of 5 GHz, the modulation frequency should be distinctly lower than the clock frequency of the data signal.

Advantageously the modulation voltage is generated by a micro-controller or micro-processor by means of PWM (Pulse-Width Modulation) or D/A converters and optional filtering.

In another embodiment, the clock modulator has a PLL which is referred to a local reference frequency. Here the PLL is not synchronized with the incoming data stream but with another, preferably stable frequency. This has the advantage that a propagation of jitter and other interference is effectively suppressed. The local reference frequency must be close to the frequency of the data stream. It is preferred to be in a range of +/−1%, and more preferred +/−200 ppm, of the frequency of the data stream. Because here slightly different data rates can occur, the clock modulator may have an intermediate memory for buffering the data. Furthermore, the clock modulator can introduce preferably redundant data or also empty data records into the data stream in case the clock frequency of the clock modulator is higher than the clock frequency of the incoming data stream. In case the clock frequency of the incoming data stream is higher than the clock frequency of the clock modulator, the clock modulator can remove preferably redundant data, or also empty data records from the incoming data stream.

For the sake of clarity of representation the present document describes a transmission from a rotating part to a stationary part. However, a transmission in the opposite direction is also possible. The embodiments are also applicable to linearly movable transmission paths or any other, even stationary, transmission paths such as conductor systems or bus systems.

With a computer tomograph described herein, data are transmitted between the rotating part 1 and the stationary part 2. At least one data source 4 is provided on the rotating part and at least one data sink 5 on the stationary part. A data source can be, for example, an X-ray detector 103 or its DAS (Data Acquisition System), or also any other control means, or a computer. The data from a plurality of data sources can be also combined with each other for transmission. A data sink can be a computer 106 for evaluating and conditioning the data, but also another control unit.

The direction of transmission has here been chosen to be that from the rotor to the stator, because this corresponds to the most usual case of application. However, transmission in the opposite direction, or even bidirectional transmission, is equally possible.

A method for transmitting data via a rotary joint includes:
(a) converting data from a data source 4 by means of a transmitter 30 to signals which are matched to the line 21, with optional clock modulation for widening the signal spectrum;
(b) transmitting the signals by means of the line 21 to a receiver 31;
(c) receiving the signals with an optical receiver 31 in the driver 22;
(d) feeding the signals from the driver 22 into the transmission line arrangement 6 of the rotary joint 3, with optional clock modulation for widening the signal spectrum;
(e) receiving the signals from the transmission conductor arrangement by means of a receiving coupler arrangement 7 and conditioning with a receiving unit 23;
(f) converting the received signals by means of a transmitter 32 to signals which are matched to a second line 24, with optional clock modulation for widening the signal spectrum;
(g) transmitting the optical signals by means of the second line 24 to a data sink 5;
(h) receiving the signals with a receiver 33 in the data sink 5.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A rotating data transmission path comprising:
a rotating part;
a stationary part; and
a rotary joint with a transmission line arrangement and a receiving coupler arrangement, for transmission of signals between the rotating part and the stationary part; with the rotating part comprising:
at least one data source with a first transmitter, for generating a digital data stream;
at least one first line for relaying the digital data stream from the first transmitter; and
at least one driver with a first receiver for receiving the digital data stream along the first line, and for controlling the transmission line arrangement;
and with the stationary part comprising:
at least one receiving unit for receiving and conditioning signals of a data stream received via the receiving coupler arrangement, having a second transmitter for retransmitting the data stream;
at least one second line for relaying the data stream retransmitted from the second transmitter; and
at least one data sink with at least one second receiver for receiving the retransmitted data stream along the second line;
wherein at least one of the data source, driver, receiving unit, and data sink comprises a clock modulator for broadening a frequency spectrum of a data clock, so that further spectral spikes occur in close proximity of individual spectral spikes of an unmodulated data clock, whereby a signal amplitude of the individual spectral spikes is reduced.

2. The rotating data transmission path according to claim 1, wherein at least one clock modulator comprises an oscillator for generating a modulated data clock, and a means for synchronizing data with the modulated data clock.

3. The rotating data transmission path according to claim 2, wherein the oscillator for generating a modulated data clock is synchronized with a local reference frequency which is not synchronized with, but nearly equal to a frequency of the clock or of unsynchronized data.

4. The rotating data transmission path according to claim 3, wherein the clock modulator comprises an intermediate data memory.

5. The rotating data transmission path according to claim 4, wherein the clock modulator is adapted to remove from the data stream or to insert therein at least one of redundant data and empty data sets.

6. The rotating data transmission path according to claim 3, wherein the clock modulator is adapted to remove from the data stream or to insert therein at least one of redundant data and empty data sets.

7. The rotating data transmission path according to claim 1, wherein at least one clock modulator has a PLL comprising a VCO, with an additional modulation signal being fed into a control voltage input of the VCO.

8. The rotating data transmission path according to claim 7, wherein feeding-in of the additional modulation signal is effected from a signal generator which is coupled to the control voltage input of the VCO via an RC-module.

9. The rotating data transmission path according to claim 7, wherein an oscillator for generating a modulated data clock is synchronized with a local reference frequency which is not synchronized with, but nearly equal to a frequency of the clock or of unsynchronized data.

10. The rotating dada transmission path according to claim 9, wherein the clock modulator comprises an intermediate data memory.

11. The rotating data transmission path according to claim 10, wherein the clock modulator is adapted to remove from the data stream or to insert therein at least one of redundant data and empty data sets.

12. The rotating data transmission path according to claim 9, wherein the clock modulator is adapted to remove from the data stream or to insert therein at least one of redundant data and empty data sets.

13. The rotating data transmission path according to claim 1, wherein at least one clock modulator comprises a PLL with a frequency divider, with a division ratio of the frequency divider being varied by a modulation signal.

14. A computer tomograph comprising a rotating data transmission path according to claim 1.

15. A method for transmitting data via a rotary joint, comprising:

converting data from a data source to signals by means of a first transmitter with optional clock modulation;

transmitting the signals by means of a first line to a driver;

receiving the signals with a first receiver in the driver;

feeding signals from the driver with optional clock modulation into a transmission line arrangement of the rotary joint;

receiving signals from the transmission line arrangement by means of a receiving coupler arrangement;

evaluating signals received by the receiving coupler arrangement in a receiving unit and converting these signals, with optional clock modulation, to signals by means of a second transmitter;

transmitting the signals by means of a second line to a data sink; and receiving the signals with optional clock modulation with a second receiver in the data sink.

* * * * *